United States Patent [19]

Bendel et al.

[11] Patent Number: 5,415,707
[45] Date of Patent: May 16, 1995

[54] HIGH MODULUS MATERIALS FOR SURGICAL NEEDLES

[75] Inventors: Lee P. Bendel, Lebanon; Lawrence P. Trozzo, Hillsborough, both of N.J.

[73] Assignee: Ethicon, Inc., Somerville, N.J.

[21] Appl. No.: 132,012

[22] Filed: Oct. 5, 1993

[51] Int. Cl.⁶ .................. C22C 27/04; A61B 17/00
[52] U.S. Cl. ............................ 148/423; 420/432; 606/222; 606/223
[58] Field of Search ............... 148/423; 420/432; 606/222, 223; 163/1, 2, 3, 4, 5

[56] References Cited

U.S. PATENT DOCUMENTS

| | | | |
|---|---|---|---|
| 2,074,474 | 3/1937 | Jedele | 420/432 |
| 3,399,981 | 9/1968 | Maykuth et al. | 148/423 |
| 3,573,903 | 4/1971 | Delgrosso | 420/432 |
| 4,197,643 | 4/1980 | Burstone et al. | 433/20 |
| 4,513,747 | 4/1985 | Smith | 128/339 |
| 4,660,559 | 4/1987 | McGregor et al. | 128/339 |
| 4,672,734 | 6/1987 | Kawada et al. | 29/517 |
| 4,799,484 | 1/1989 | Smith et al. | 128/339 |
| 4,828,547 | 5/1989 | Sahi et al. | 604/110 |
| 4,883,469 | 11/1989 | Glazier | 604/192 |
| 4,883,471 | 11/1989 | Braginetz et al. | 604/195 |
| 4,905,695 | 3/1990 | Bendel et al. | 606/222 |
| 4,927,420 | 5/1990 | Newkirk et al. | 606/45 |
| 5,000,912 | 3/1991 | Bendel et al. | 420/34 |
| 5,041,041 | 8/1991 | Passmore et al. | 445/48 |
| 5,100,432 | 3/1992 | Matsutani | 606/283 |
| 5,123,910 | 6/1992 | McIntosh | 606/223 |
| 5,258,013 | 11/1993 | Granger et al. | 606/223 |

FOREIGN PATENT DOCUMENTS 1243279 8/1971 United Kingdom ............... 420/432

OTHER PUBLICATIONS

Abidin et al., Biomechanics of Curved Surgical Needle Bending, J. Biomed. Mater. Res. Appl. Biomaterials, vol. 23, No. A1, 129–143, (Dec. 1989).
Bendel et al., Ophtalmic Needles, *Ophthalmology*, vol. 93, No. 9, (Sep. 1986). pp. 61–64.
McClung et al., Biomechanical Performance of Ophthalmic Surgical Needles, *Ophthalmology*, vol. 99, No. 2 (Feb. 1992). pp. 232–237.
Pavlovich, Lucas J., et al., A Synthetic Membrane for Testing Needle Penetration, *Journal of Applied Biomaterials*, vol. 4, 157–160 (Dec. 1993).
Bendel, Lee P., et al., Tensile & Bend Relationships of Several Surgical Needle Materials, *Journal of Appl. Biomaterials*, vol. 4, 161–167 (Dec. 1993).
Shunk, Francis A., Constitution of Binary Alloys, second supplement, McGraw-Hill, 1969, pp. 648–649.

Primary Examiner—Scott Kastler
Assistant Examiner—Sikyin Ip
Attorney, Agent, or Firm—Emil Richard Skula

[57] ABSTRACT

Disclosed are sterile surgical needles formed of alloys of tungsten and a second metal selected from the group consisting of rhenium, rhodium and iridium. The needles exhibit a tensile yield strength in excess of 250,000 psi and a tensile modulus of elasticity in excess of $45 \times 10^6$ psi, and have advantageously high ductility. The needles have a body portion, a distal point, and a proximal suture mounting portion. Preferably the needles comprise about 3 to about 6 weight percent of rhenium, rhodium and/or iridium. The needles exhibit improved yield point and elastic modulus in tension.

22 Claims, 2 Drawing Sheets

HIGH MODULUS MATERIALS FOR SURGICAL NEEDLES

BACKGROUND OF THE INVENTION

The present invention relates to surgical needles, and in particular to needles having a desirably high combination of stiffness, bend strength and ductility.

Surgical needles have been known for some time and such needles with sutures attached are commonly used in various types of surgical procedures. The surgical needles are usually made from stainless steel and have a blunt end to which a suture is attached. The blunt end may be drilled or have a channel placed therein and the suture is usually swaged or crimped in the drilled hole or channel. In order to reduce trauma in placing sutures in tissue, the suture itself generally has a diameter less than the diameter of the needle. Also, the point and cutting edge of the needle should be made as sharp as possible so as to require as little force as possible to penetrate the tissue and place the suture and consequently to cause the least amount of trauma to the sutured area.

Surgical needles are straight or curved, that is, they have the shape of some part of a circle. This may be from a quarter of a circle to five-eighths of a circle. At one end of the needle is the point or the extreme tip of the needle. The section from that point to the maximum width of the needle is termed the "blade" of the needle. In cutting needles, the blade includes the cutting edge from the point towards the blunt end. Behind the cutting edge is the body portion of the needle; that is, the area of the needle to be grasped by an appropriate needle holder. At the blunt end of the needle is the swage or the portion of the needle into which the suture is inserted and affixed. In placing the needle, the needle is grasped by a suitable needle holder which usually is a forceps type instrument that grasps the needle at the body portion with sufficient force to insure that the needle will not move or turn in the instrument when the needle is being placed by the surgeon.

Use of a needle can exert stressing forces on the needle, since the force used to drive the needle into and through tissue (e.g., a blood vessel, the cornea of the eye, and the like) needs to be sufficient to drive the needle and overcome frictional drag through the tissue. Applying this force along the shaft of the needle from the point at which the needle is held risks causing the needle to flex, which is undesirable as it causes loss of control of the needle. This means the body portion of the needle should have a relatively high stiffness, that is, a low tendency to flex and high tendency retain its configuration when subjected to a deforming force. The needle should also not be brittle; if the body is too brittle it may break during use if too much force is placed on the needle during its use. The needle should also be ductile.

The cutting edge and the point of the needle should also be as sharp as possible. The harder the needle the sharper it can be made. The sharper the needle, the less force required to make the initial penetration and the less the drag by the needle body during the remainder of the passage of the needle through tissue. Generally speaking, to make a sharp needle one needs a very hard metal; however, the harder the metal the more brittle it becomes and the greater the chance it will be broken by the needle holding instrument or during placement.

The desirable bend properties for a surgical needle are high stiffness, strength, and ductility in order to penetrate tissue which is being sutured without undue flexing, bending, or breaking during the surgical procedure. Flexing is described as the elastic (or temporary) deflection of the needle out of its original curvature. Stiffness is characterized by the bend modulus which is the slope of the linear-elastic portion of the load-deflection curve. Bending is described as the occurrence of plastic (or permanent) deformation. Strength is characterized by the surgical yield strength which is the point at which the load deflection curve departs from linearity. The surgical yield strength is determined in accordance with the techniques described in Bendel, L. and Trozzo, L., "Tensile and Bend Relationships of Several Surgical Needle Materials", J. of Applied Biomaterials, Vol. 4, pp 161-167 (1993). Breaking is described as the separation of the needle into two pieces. Ductility is characterized as the ability to bend without breaking.

Surgery, especially microsurgery, requires that the needle's path be closely controlled. If the needle flexes or bends as it enters the tissue (or as it pierces the inner surface of e.g., a blood vessel or cornea before reemerging) there can result improper placement of the needle and suture, and serious trauma to the tissue and the patient. Microsurgery necessarily involves the use of needles of exceedingly small diameter, yet the need for high strength is all the more compelling even as the difficulty of obtaining high strength and high stiffness increases due to the very small dimensions of the needle.

The design techniques generally employed to achieve the described properties of strength and stiffness are often in conflict, however. One straightforward approach to improve the strength of a needle, for instance, is to increase its diameter, or thickness. But by increasing the thickness of the needle, the force necessary to penetrate the tissue is also increased, and the opening left in the tissue after passage of the needle is also enlarged. Likewise, penetration ease can be improved by making the needle thinner, but this approach can risk correspondingly reducing the needle's strength and stiffness. Thus, the design of a needle with favorable performance often requires that a tradeoff be made between size and properties. Bend properties, such as stiffness and surgical yield strength are related to the needle geometry and the material tensile properties: tensile modulus of elasticity and tensile yield strength. Arriving at a satisfactory combination of high strength, high stiffness, and good ductility though, has proven notably elusive.

In general, surgical needles of the type described have been made of various stainless steels. Exemplary of such steels are AISI Type 420 stainless steel and ASTM 45500 stainless steel. The assignee of the present invention also markets needles under the name ETHALLOY, and has disclosed stainless steel compositions useful in making surgical needles in its U.S. Pat. No. 5,000,912. Attempts to develop satisfactory combinations of properties have centered around adjusting the alloy elements of the stainless steel used therein.

Consideration of other materials from which surgical needles might be fabricated is problematic because of the inability to predict whether a composition would exhibit a favorable combination of properties from knowledge of the properties of its components. For instance, tungsten is considered to have a high tensile modulus of elasticity but a relatively moderate tensile yield strength and ductility. On the other hand, noble metals including rhenium, rhodium and iridium (among others) which have a high tensile modulus of elasticity are considered not to have high tensile yield strengths.

There is thus a need for surgical needles of novel composition which permit the economical fabrication of needles and the realization of the properties described herein in combination to a degree superior to those presently available.

SUMMARY OF THE INVENTION

It has now been discovered that sterile surgical needles having a high stiffness and a high surgical yield strength and good ductility can be formed from tungsten or a tungsten alloy containing up to about 30% by weight of one or more metals selected from the group consisting of rhenium, rhodium and iridium. In a preferred embodiment, the sterile surgical needle of the present invention is drawn to a diameter of 0.0010" to 0.060".

DETAILED DESCRIPTION OF THE INVENTION

Figure 1:
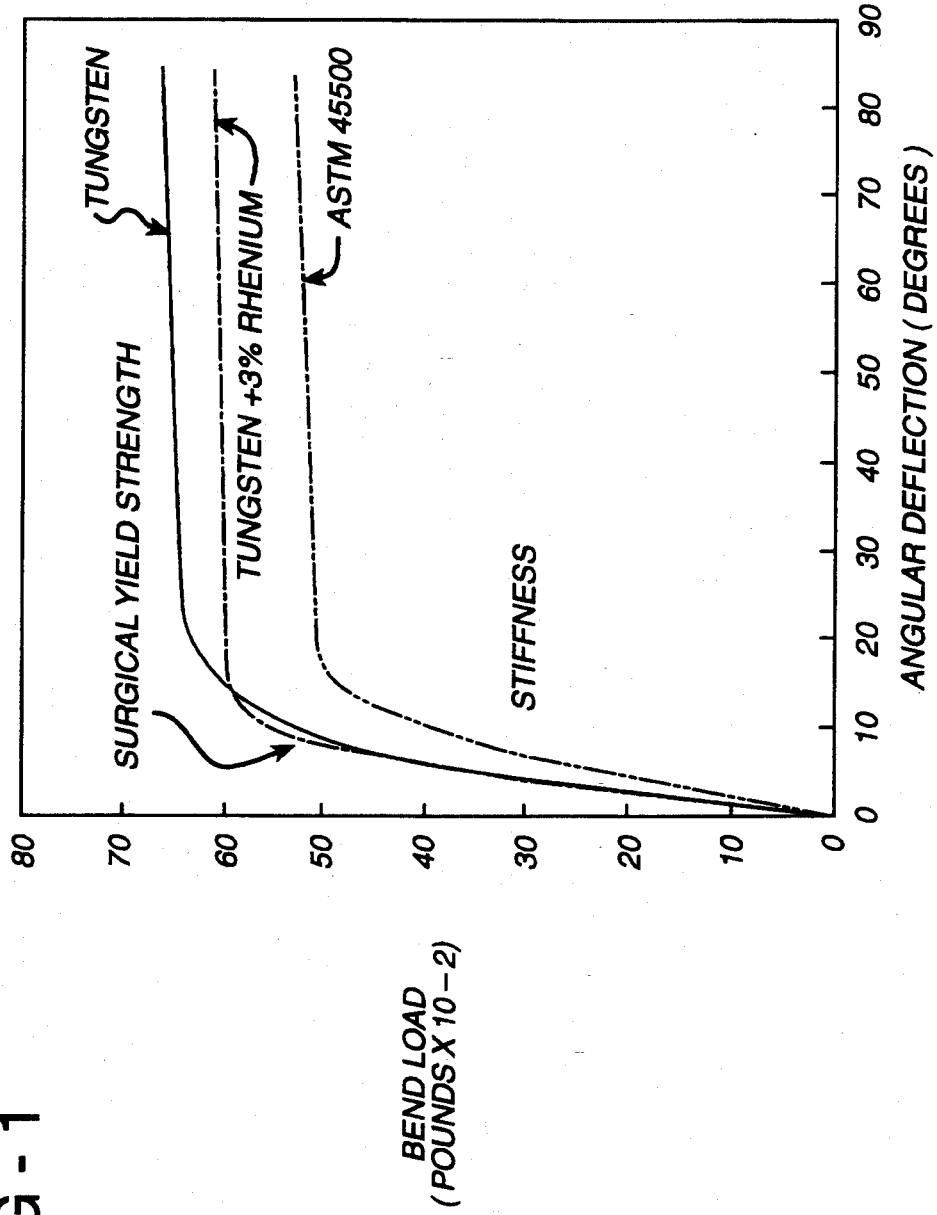
FIG. 1 is a graph of load versus bend angle for three surgical needle compositions.

In composition, the sterile surgical needles of the present invention are formed from tungsten or an alloy of tungsten and a second component which is rhenium, rhodium, iridium, or two or all three of rhenium, rhodium and iridium. Preferably, no more than trace amounts of other elements are present, and more preferably the needle contains only tungsten and the second metal. The second component comprises up to about 30 wt. % of the alloy, and more preferably about 3 to about 6%. Satisfactory results have been obtained with alloys wherein the second component is present in an amount of about 3 wt. %

The needle will have a diameter effective to permit satisfactory usage in fine surgery. Typically, the diameter will be less than about 60 mils (thousandths of an inch), preferably less than about 15 mils, down to about 1 mil, and preferably about 1.4 to about 12 mils. It will be recognized that the needle can have the conventional circular cross-section, and that the needle may instead be of non-circular cross-sectional shape such as triangular; trapezoidal; rectangular; hexagonal; elliptical; or rectangular wherein the opposed shorter ends of the rectangle are rounded into semicircles. By "diameter" herein is meant the square root of $(4A/\pi)$ where A is the cross-sectional area. The needle can be provided with a "ribbon" shape, or a rectangular or "I-beam" shape, or with a cross-section which smoothly undergoes transition from the point to a circular cross-section, to a rectangular cross-section having rounded and then sharper corners, as described in U.S. Pat. No. 4,799,484.

The point can be a conventional tapered point. It can instead be a blunt point such as that described in U.S. Pat. No. 5,123,910, a point having converging cutting edges as described in U.S. Pat. No. 4,513,747, or any other point effective to promote smooth penetration into and passage through the tissue. The manner in which the needle is provided with the point of choice is quite familiar to the needle manufacturer.

The needle can be straight but preferably is curved through a radius of curvature which need not be constant but is preferably constant. Thus, more preferred shapes of the needles of the present invention comprise sections of a circle, such as a quarter circle, three-eighths circle, half circle, or five-eighths of a circle. As indicated above, the needle can comprise means at or near the blunt end furthest from the point, for securing a suture to the end of the needle. That means may comprise, for instance, a slot or channel in the outer surface of the needle or an opening in the end of the needle which is then swaged to hold the end of the suture.

The surgical needles of the present invention are characterized by a unique combination of high stiffness, high bend strength and good ductility, which terms are defined hereinabove. For the needles of the present invention, the wire tensile yield strength is generally at least about 250,000 psi. A high tensile yield strength is useful as it reflects higher bend strength and indicates the ability of the needles of the present invention to withstand potentially deforming stresses without suffering permanent deformation.

For the needles of the present invention the wire also exhibits uniquely high tensile modulus of elasticity. For needles of the present invention, the wire tensile modulus of elasticity is generally at least about $45 \times 10^6$ psi. The high tensile modulus of elasticity is desirable in that it reflects higher stiffness and the ability of the needles of the present invention to withstand potentially deforming stresses by retaining their shape, without undue flexing.

For the needles of the present invention the wire percent elongation in tension is generally at least 2%. A high percent elongation is useful as it reflects higher ductility and indicates the ability of the needles of the present invention to withstand bending during use without suffering breakage. The needles of the present invention are also highly resistant to corrosion. High resistance to corrosion is useful as it indicates the ability of the needles of the present invention to withstand the corrosive effects of sterilization processes without corroding.

Referring to FIG. 1, there is depicted the relationship of load to bend angle to compare two needles of composition in accordance with the present invention to a commercial stainless steel needle formed from ASTM 45500 alloy stainless steel. From the three curves the improvement in bend strength can be ascertained, as can the fact that the composition of the present invention has a significantly higher stiffness at the loads likely to be encountered in normal surgical use. Additionally, the composition of the present invention was able to withstand 84° of bending without breakage, providing a safety factor for the surgeon should the needle be subjected to an excessive force resulting in bending during surgical use. The two samples were tested as set forth in Example 1.

The needles of the present invention can be fabricated by processing the starting metal or alloy to normal mill standards to a size about 50% in area larger than the desired final size, annealing, and cold drawing to the finished size. The resulting wire is then cleaned free of surface oxides and other surface contaminants. Wire suitable as a starting material for making the needles of this invention is commercially available.

Following the final drawing to the final desired diameter, one end of the needle is given a point having the desired shape, the point being provided by any conventional technique such as grinding. Alternatively, the needle can be provided with a hardened point and cutting edge by exposing it to a laser beam or electron beam, as taught in U.S. Pat. No. 4,660,559. The opposite end of the needle is given an opening in its end, or other means by which the end of a suture can be attached to the needle by swedging or the like.

The needle is then given its desired curvature, typically by rolling around a mandrel of the desired radius of curvature.

The needle can be provided with a coating, for instance, a polymeric coating, in accordance with known techniques, if desired. The needle is then packaged and the needle, suture and package are sterilized, again in accordance with conventional techniques.

In use, a suture is attached to the blunt unpointed end of the needle. Then, the needle can be manipulated by hand or preferably can be gripped in an appropriate needle holder and then used in the desired surgical procedure.

The sterile surgical needles of the present invention will be illustrated in the following examples, which are provided for purposes of illustration and should not be interpreted as limiting in any way the scope of the claims appended hereto.

EXAMPLE 1

Figure 2:
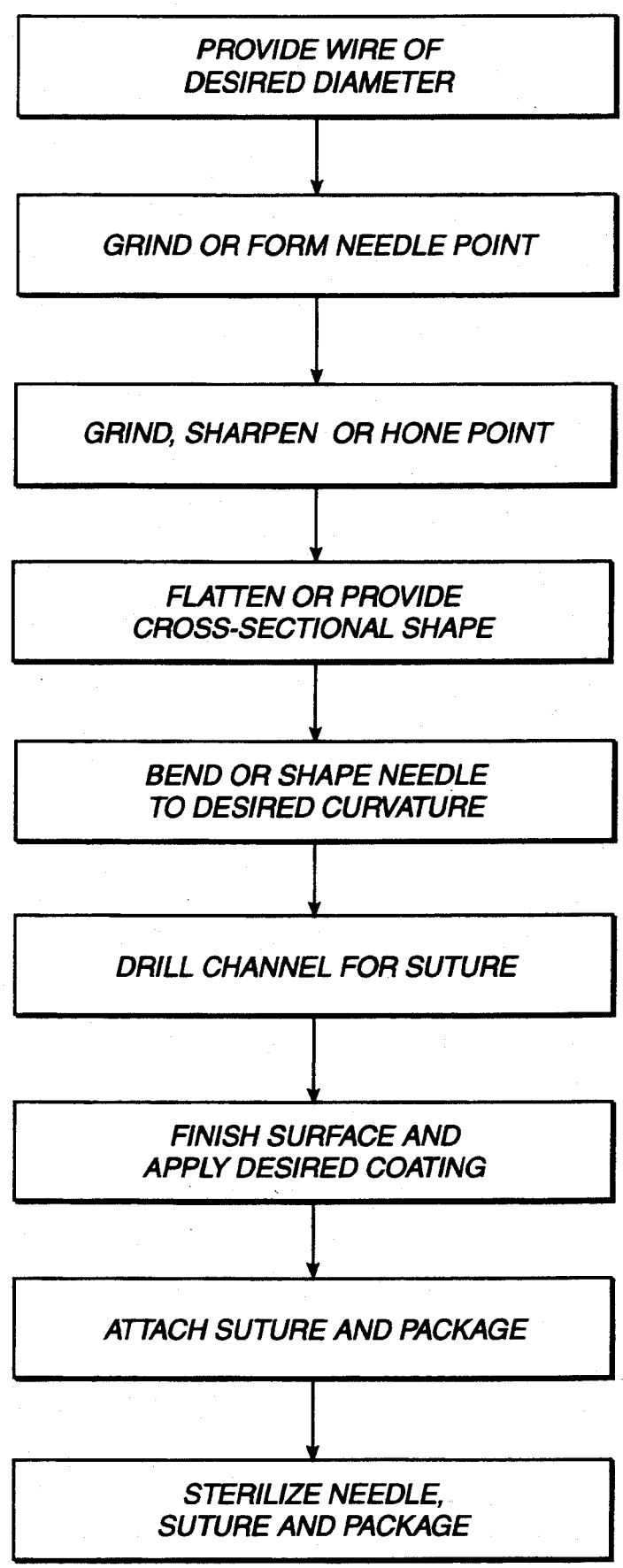
FIG. 2 is a block diagram showing the steps in the production of needles in accordance with the present invention.

Straight needles were fabricated in accordance to the block diagram shown in FIG. 2. Bend tests were conducted of needles from the present invention made from two compositions: tungsten wire, and tungsten-3%-rhenium wire, both in 10 mil finished diameters. Bend tests were also conducted of needles made from commercially available ASTM 45500 alloy stainless steel wire in a 10 mil finished diameter.

The bend tests were conducted using apparatus detailed in the aforementioned article, "Tensile and Bend Relationships . . . ", the teachings of which are hereby incorporated herein by reference. Fixtured needles were bent through a total of 84 degrees deflection. A moment arm of 0.100 inches was used. Load applied to each needle was continuously measured electronically. A permanent chart recording was thus produced showing load, (Y-axis in pounds), as a function of bend angle, (X-axis in degrees). FIG. 1 shows the results from all three test needles.

Needle stiffness, the resistance to flexing, was characterized by the bend modulus. The slope of the linear-elastic straight-line portion of the load/deflection curve defines the bend modulus. The first 10 degrees of deflection generally comprise the straight-line portion of the bend test for surgical needle materials. A high bend modulus thus indicates that greater forces can be supported and less flexing will result. For tungsten needles of the present invention, the bend modulus is 0.071 pounds per degree. For tungsten-3%-rhenium needles the bend modulus is 0.073 pounds per degree. For ASTM grade 45500 alloy stainless steel needles the bend modulus is only 0.042 pounds per degree. Needles of the present invention thus show about 70% higher stiffness than do needles of the commercial needle material.

Needle bending, or permanent deformation, occurs with more load in a strong material. Resistance to bending is characterized by the surgical yield strength. The yield strength is measured at the onset of permanent deformation, which is the point at which the load/deflection curve departs from linearity. During surgery, the first visually noticeable needle deformation occurs at about 2° beyond the yield point. This is called the surgical yield point, and is defined as the intersection with a line constructed 2 degrees offset, parallel to the linear-elastic portion of the load/deflection curve. A high surgical yield strength thus indicates that greater forces can be supported before there is any permanent shape change to the needle. For tungsten needles of the present invention, the surgical yield strength is 0.526 pounds. For tungsten-3%-rhenium needles the surgical yield strength is 0.540 pounds. For ASTM grade 45500 alloy stainless steel the surgical yield strength is 0.462 pounds. Needles of the present invention thus show about 15% higher strength than do needles of the commercial needle alloy.

What is claimed is:

1. A sterile surgical needle having a high tensile modulus of elasticity and a high tensile yield strength, said needle comprising a body portion, a distal point and a proximal suture mounting portion, said needle further comprising a tungsten alloy consisting essentially of about 3% to about 6% by weight of one or more metals selected from the group consisting of rhenium, rhodium and iridium the balance tungsten and incidental impurities.

2. A sterile surgical needle is claimed in claim 1 in which said second metal comprises rhenium.

3. A sterile surgical needle as claimed in claim 2 in which said alloy comprises 3% rhenium.

4. A sterile surgical needle as claimed in claim 2 in which said needle has a tensile modulus of elasticity in excess of $45 \times 10^6$ psi.

5. A sterile surgical needle as claimed in claim 2 in which said needle has a tensile yield strength in excess of 250,000 psi and a tensile modulus of elasticity in excess of $45 \times 10^6$ psi.

6. A drawn sterile surgical needle as claimed in claim 1, 4 or 5.

7. A sterile surgical needle as claimed in claim 6 in which said needle is drawn to a diameter of 0.0010" to 0.060".

8. A sterile surgical needle as claimed in claim 6 in which said needle is drawn to a diameter of 0.0010" to 0.015".

9. A sterile surgical needle as claimed in claim 1 in which said second metal comprises rhodium.

10. A sterile surgical needle as claimed in claim 9 in which said alloy comprises 3% rhodium.

11. A sterile surgical needle as claimed in claim 9 in which said needle has a tensile modulus of elasticity in excess of $45 \times 10^6$ psi.

12. A sterile surgical needle as claimed in claim 9 in which said needle has a tensile modulus of elasticity in excess of $45 \times 10^6$ psi and a tensile yield strength in excess of 250,000 psi.

13. A drawn sterile surgical needle as claimed in claim 9, 11 or 12.

14. A sterile surgical needle as claimed in claim 13 in which said needle is drawn to a diameter of 0.0010" to 0.060".

15. A sterile surgical needle as claimed in claim 13 in which said needle is drawn to a diameter of 0.0010" to 0.015".

16. A sterile surgical needle as claimed in claim 1 in which said second metal comprises iridium.

17. A sterile surgical needle as claimed in claim 16 in which said alloy comprises 3% iridium.

18. A sterile surgical needle as claimed in claim 16 in which said needle has a tensile modulus of elasticity in excess of $45 \times 10^6$ psi.

19. A sterile surgical needle as claimed in claim 16 in which said needle has a tensile modulus of elasticity in excess of $45 \times 10^6$ psi and a tensile yield strength in excess of 250,000 psi.

20. A drawn, annealed sterile surgical needle as claimed in claim 16, 18 or 19.

21. A sterile surgical needle as claimed in claim 20 in which said needle is drawn to a diameter of 0.0010" to 0.060".

22. A sterile surgical needle as claimed in claim 20 in which said needle is drawn to a diameter of 0.0010" to 0.015".

* * * * *